United States Patent
Weber (10) Patent No.: US 10,401,280 B2
(45) Date of Patent: Sep. 3, 2019

(54) LIGHT GUIDE FOR FLUID TESTING CELLS

(71) Applicant: HEWLETT-PACKARD DEVELOPMENT COMPANY, L.P., Houston, TX (US)

(72) Inventor: Timothy L. Weber, Corvallis, OR (US)

(73) Assignee: Hewett-Packard Development Company, L.P., Spring, TX (US)

(*) Notice: Subject to any disclaimer, the term of this patent is extended or adjusted under 35 U.S.C. 154(b) by 0 days.

(21) Appl. No.: 15/570,958

(22) PCT Filed: Jul. 24, 2015

(86) PCT No.: PCT/US2015/041896
§ 371 (c)(1),
(2) Date: Oct. 31, 2017

(87) PCT Pub. No.: WO2017/018977
PCT Pub. Date: Feb. 2, 2017

(65) Prior Publication Data
US 2018/0113068 A1 Apr. 26, 2018

(51) Int. Cl.
*G01N 21/05* (2006.01)
*G01N 21/11* (2006.01)
(Continued)

(52) U.S. Cl.
CPC .......... *G01N 21/05* (2013.01); *B01L 3/50273* (2013.01); *G01N 21/11* (2013.01);
(Continued)

(58) Field of Classification Search
CPC ..... B01L 2300/0816; B01L 2400/0442; B01L 3/50273; B81B 1/00; B81B 7/02; G01N 2021/0328; G01N 2021/0346; G01N 2021/6439; G01N 2021/7783; G01N 2021/7786; G01N 21/05; G01N 21/11; G01N 21/59
USPC ................................................. 356/432–448
See application file for complete search history.

(56) References Cited

U.S. PATENT DOCUMENTS 4,558,946 A * 12/1985 Galle ..................... G01N 35/02
356/318
5,818,580 A 10/1998 Murnick
(Continued)

FOREIGN PATENT DOCUMENTS

DE 102007021544 A1 11/2008
WO WO-0045051 A2 8/2000
WO WO-2014178827 11/2014

OTHER PUBLICATIONS

Carona, G.N.V. et al., Analysis of Bacterial Function by Multicolour Fluorescence Flow Cytometry and Single Cell Sorting, (Research Paper), Sep. 2000.
(Continued)

*Primary Examiner* — Tri T Ton
(74) *Attorney, Agent, or Firm* — Perry + Currier Inc (57) ABSTRACT

In one example, testing cells extend along a length of a slot. Each testing cell includes a microfluidic channel extending from the slot, a pump to move fluid from the slot into the channel, a discharge nozzle through which fluid exits the channel, a fluid discharger to discharge fluid from the channel through the nozzle and a photosensor. A light guide is provided to receive light from an external light source and is to serially transmit the light to the microfluidic channel of each of the plurality of testing cells.

18 Claims, 6 Drawing Sheets

(51) Int. Cl.
- *B01L 3/00* (2006.01)
- *G01N 21/59* (2006.01)
- *G01N 21/64* (2006.01)
- *G01N 21/77* (2006.01)
- *G01N 21/03* (2006.01)

(52) U.S. Cl.
CPC ......... *G01N 21/59* (2013.01); *G01N 21/6428* (2013.01); *B01L 2300/0816* (2013.01); *B01L 2400/0442* (2013.01); *G01N 2021/0328* (2013.01); *G01N 2021/0346* (2013.01); *G01N 2021/6439* (2013.01); *G01N 2021/7783* (2013.01); *G01N 2021/7786* (2013.01); *G01N 2201/024* (2013.01); *G01N 2201/0221* (2013.01); *G01N 2201/0873* (2013.01)

(56) References Cited

U.S. PATENT DOCUMENTS

| | | | |
|---|---|---|---|
| 7,491,552 | B2 | 2/2009 | McDevitt et al. |
| 8,129,179 | B2 | 3/2012 | Wikswo et al. |
| 8,163,538 | B2 | 4/2012 | Woudenberg et al. |
| 8,349,616 | B2 | 1/2013 | Schulz et al. |
| 8,486,247 | B2 | 7/2013 | Kayyem |
| 8,750,652 | B2 | 6/2014 | Butte et al. |
| 2006/0160209 | A1 | 7/2006 | Larson |
| 2008/0213821 | A1 | 9/2008 | Liu et al. |
| 2009/0064276 | A1* | 3/2009 | Dugas ............ G01N 35/00732 726/2 |
| 2012/0071342 | A1 | 3/2012 | Lochhead et al. |
| 2013/0203157 | A1* | 8/2013 | Cheung ............ G01N 15/0612 435/286.5 |
| 2014/0130745 | A1* | 5/2014 | Van Halsema ........... A01J 5/01 119/14.08 |
| 2014/0219870 | A1* | 8/2014 | Ryu ................. B01L 3/502715 422/69 |
| 2015/0057194 | A1 | 2/2015 | McCaffrey et al. |
| 2018/0113068 | A1* | 4/2018 | Weber ...................... B81B 1/00 |

OTHER PUBLICATIONS

Wooseok Jung Et al, Point-of-care testing (POCT) diagnostic systems using microfluidics lab-on-a-chip technologies, Microelectronic Engineering vol. 132 ( Oct. 2014 pp. 46-57 XP055539476.

\* cited by examiner

LIGHT GUIDE FOR FLUID TESTING CELLS

BACKGROUND

Various sensing devices are currently available for sensing different attributes of fluid, such as blood, as an example. Such sensing devices are often large, complex and expensive.

DETAILED DESCRIPTION OF EXAMPLES

Figure 1:
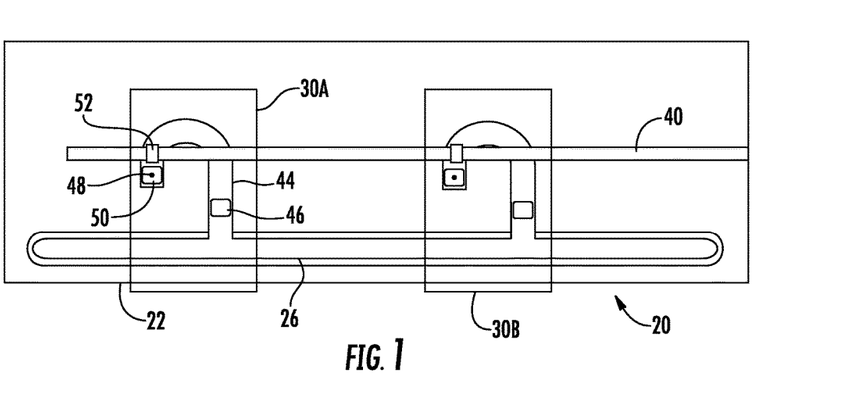
FIG. 1 is a schematic diagram of an example fluid testing device.

FIG. 1 schematically illustrates an example fluid testing device 20. As will be described hereafter, fluid testing device 20 comprises multiple distinct testing cells which receive fluid samples from a single source, facilitating multiple measurements per sample for enhanced accuracy or multiple different measurements per sample. Fluid testing device 20 comprises body 22, slot 26, testing cells 30A, 30B (collectively referred to as testing cells 30) and light guide 40. Body 22 comprises a structure in which slot 26 is formed. In one implementation, body 22 comprises a circuit chip having a substrate, such as silicon, upon which slot 26 and electronic componentry and electrical conductors or traces are provided. In one implementation, body 22 is part of cassette that is to be removably connected to a computing device, directly or indirectly, wherein the computing device controls the operation of cells 30 and analyzes data from cells 30.

Slot 26 comprises a fluid passage connected to an input of each of cells 30 Slot 26 is connected to a fluid sample input, wherein fluid to be tested or analyzed is supplied to slot 26 through the fluid sample input and wherein slot 26 supplies at least portions of the fluid sample to the cells 30. For purposes of this disclosure, the term "fluid" comprises the analyte in or carried by the fluid such as a cell, particle or other biological substance.

Cells 30 comprise distinct units along a length of slot 26, wherein the length is along a major dimension of slot 26. Cells 30 carry out distinct measurements or tests upon fluid samples provided through slot 26. Although device 20 is illustrated as comprising two cells 30, in other implementations, device 20 may comprise greater than two cells 30 along one side of slot 26. Although device 20 is illustrated as comprising cells 30 on one side of slot 26, in other implementations, additional cells 30 may be located on the other side of slot 26.

As shown by FIG. 1, each of cells 30 comprises microfluidic channel 44, pump 46, discharge passage 48, fluid discharger 50 and photosensor 52. Microfluidic channel 44 comprises a fluid passage extending from or branching off of slot 26. In one implementation, microfluidic channels 44 of cells 30 are similarly sized. In another implementation, microfluidic channel 44 of cells 30 are differently sized, having different cross-sectional areas or differently sized constrictions. In such implementations, the smaller sized channel 44 inhibits entry from slot 26 of cells or particles that are too large such that the smaller size may channel serves as a filter to restrict what type or size of cells or molecules are being sensed by the particular testing cell 30.

Pump 46 comprises a device situated in or along microfluidic channel 44 to pump or move fluid into channel 44 from slot 46. In one implementation, pump 46 comprises a bubble jet inertial pump. In such an implementation, the bubble jet inertial pump produces an initially expanding bubble to move or drive adjacent fluid away from the bubble. One example of a bubble jet pump comprises a micro-heater, such as a thermal inkjet (TIJ) pump. A TIJ pump may utilize at least one electrical resistor through which electric current is passed. The heat produced by the at least one resistor as electric current passes through the at least one resistor may vaporize or nucleate the fluid that is proximate to the resistors to create a bubble. As this bubble is initially created and expands, the bubble may initially drive adjacent fluid away from the bubble. The bubble jet inertial pump may be located along channel 44 proximate to a slot 26 and distant to a discharge passage 48. In other words, the inertial pump is spaced from the slot 26 by a distance less than one half of the length of the total fluid path between the slot 26 and discharge passage 48 or another fluid interaction component. Inertial pump may utilize inertia and momentum within channel 44 that is relatively narrow compared to the two reservoirs it connects to produce fluid flow. For purposes of this disclosure, the term "inertial pump" refers to a pumping device that initially drives fluid in both directions within a channel that is relatively narrow to the reservoirs it connects, but wherein the pumping device is asymmetrically positioned between the reservoirs such that the end result is fluid being driven in a direction towards the most distant of the two reservoirs.

In another implementation, pump 46 may comprise other pumping devices. For example, in another implementation, pump 46 may comprise a piezo-resistive inertial pump that changes shape or vibrates in response to applied electrical current to move a diaphragm to thereby move adjacent fluid from slot 26 into microfluidic channel 44. In yet other implementations, pump 160 may comprise other microfluidic pumping devices in fluid communication with microfluidic channel 44 and discharge passage 48.

Discharge passage 48 comprises a fluid conduit through which the fluid sample is discharged from channel 44. In one implementation, discharge passage 48 directs or guides fluid to a waste reservoir or other destination distinct from slot 26. In yet other implementations, discharge passage 48 directs or guides fluid to other microfluidic channels or passages of additional testing devices. In still other implementations, discharge passage 48 directs or guides fluid into trays, partitioned containers or onto a test strip and interacts with the received fluid to indicate characteristics of the received fluid. In one implementation, discharge passage 48 comprises a nozzle through which fluid is uni-directionally ejected from passage 44. In another implementation, discharge passage 48 comprises a valve through which fluid is selectively guided or ejected.

Fluid discharger 50 comprises a device to selectively move and discharge the fluid sample from channel 44 through discharge passage 48. In one implementation, fluid discharger 50 comprises a drop-on-demand fluid ejection device such as a thermal inkjet resistor which nucleates fluid to create a bubble to forcefully expel or eject fluid through discharge passage 48. In another implementation, fluid discharger 50 comprises a drop on demand fluid ejection device such as a piezo resistive device that changes shape or vibrates in response to applied electrical current to move a diaphragm to thereby eject adjacent fluid through discharge passage 48. In still other implementations, fluid discharger 50 may comprise other devices to selectively and forcibly eject fluid through discharge passage 48.

Photosensor 52 comprises an optical sensor situated in or along microfluidic channel 44. Photosensor 52 senses interaction of light with the analyte and/or solution containing the analyte within channel 44. In response to sense interactions of light with the analyte or solution, photosensor 52 outputs electrical signals which vary based upon such interactions, wherein the electrical signals are analyzed and indicate characteristics of the fluid sample that interacted with a light. Although not illustrated, each of pump 46, fluid discharger 50 and photosensor 52 receive and/or send electrical signals via electric conductive traces integrated into or supported by body 22.

Light guide 40 comprises a light guiding and directing structure that is to receive light from an external light source serially transmit light or electromagnetic radiation to the microfluidic channel of each of the testing cells 30, wherein the transmitted light passes from one cell to the next. In the example illustrated, each of testing cells 30 are sufficiently aligned with one another such that light guide 40 extends across each of such microfluidic channels 44, providing light or electromagnetic radiation to each of cells 30 for interacting with the fluid contained within each of cells 30 and for detection by photosensors 52. Because light guide 40 supplies electromagnetic radiation or light to each of the multiple cells 30, real estate upon the chip or other structure body 22 is conserved, allowing device 20 to be more compact. In addition, the complexity and cost of device 20 may also be reduced through the use of a single light guide 40 supplying light to each of the individual testing cells 30.

In the example illustrated, light guide 40 comprises a waveguide or light pipe that linearly extends across microfluidic channel 44 of each of its associated testing cells 30. As a result, device 20 is more compact. In other implementations, light guide 40 may extend in a serpentine fashion or a bent or arcuate fashion when serially extending from one fluid testing cell 30 to another fluid testing cell 30.

Figure 2:
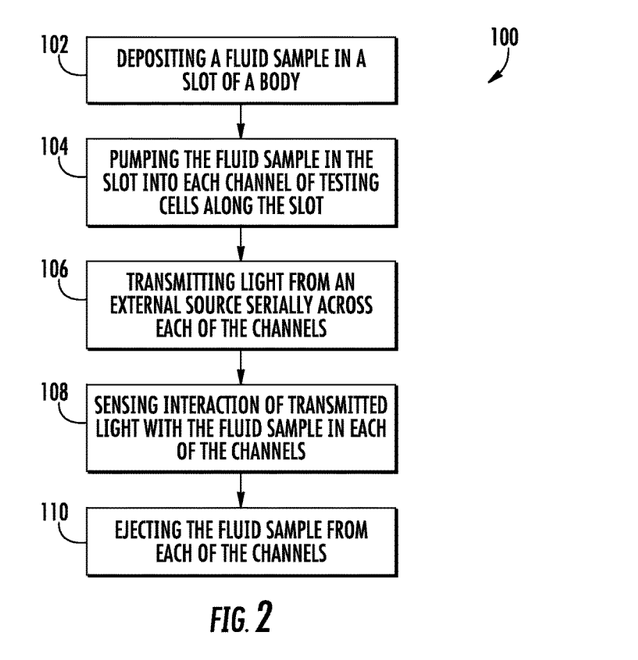
FIG. 2 is a flow diagram of an example method for testing a fluid sample using the fluid testing device of FIG. 1.

FIG. 2 is a flow diagram of an example method 100 for the use of fluid testing device 20. As indicated by block 102, a fluid sample containing an analyte to be tested, such as cells are particles, deposited into slot 26 of body 22. As indicated by block 104, pump 46 of each cell 30 pumps the fluid sample in slot 26 into a respective microfluidic channel 44 of the respective testing cell 30. As indicated by block 106, light guide 40 transmits light from an external light source serially across each of channels 44 of each of cells 30. As indicated by block 108, photosensor 52 senses interaction of the transmitted light with the fluid sample within the respective microfluidic channel 44. Photosensor 52 outputs electrical signals which vary based upon the senses interaction. Such electrical signals may then be analyzed to identify characteristics of the fluid sample within each of channels 44 of each of cells 30. As indicated by block 110, fluid discharger 50 ejects the sensed and analyzed fluid sample from the respective microfluidic channel 44 through discharge passage 48. In one implementation, the fluid is ejected to a destination distinct from slot 26.

Figure 3:
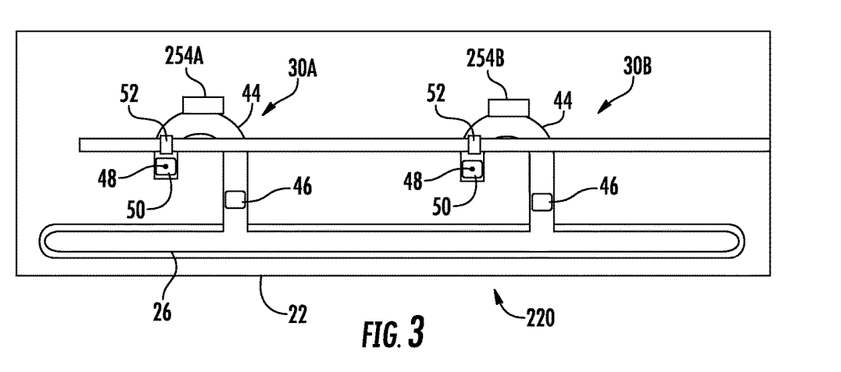
FIG. 3 is a schematic diagram of another example fluid testing device.

FIG. 3 schematically illustrates fluid testing device 20, an example implementation of fluid testing device 20. Fluid testing device 220 is similar to fluid testing device 20 except that fluid testing cells 30A, 30B additionally comprise fluid tagging dispensers 254A, 254B (collectively referred to as tagging dispensers 254). Those remaining components or elements of device to 20 which correspond to elements or components of device 20 are numbered similarly.

Fluid tagging dispensers 254 may comprise devices located along microfluidic channels 44 that dispense tags to mark particular cells or molecules of interest. In the example illustrated, dispensers 254 are located upstream of photosensor 52, between photosensor 52 and the inlet of microfluidic channel 44 adjacent slot 26. In one implementation, fluid tagging dispensers 254 dispense fluorescent powder which tags molecules of interest. Such tagging may facilitate reading by photosensor 52, wherein the light being transmitted by light guide 40 excites fluorescent powder or tags to facilitate detection by photosensor 52. In one implementation, each of dispensers 254 dispense a different fluorescent marker to differently tag different molecules, particles or cells, facilitating multiple different tests being performed at the same time the same initial sample supplied to slot 26. In another implementation, dispensers 254 dispense the same fluorescent marker. In one implementation, pumps 46 concentrate the fluid samples within microfluidic channel 44 before ejection to facilitate gathering of a sufficient amount or number of tagged molecules for sensing and analysis.

Figure 4:
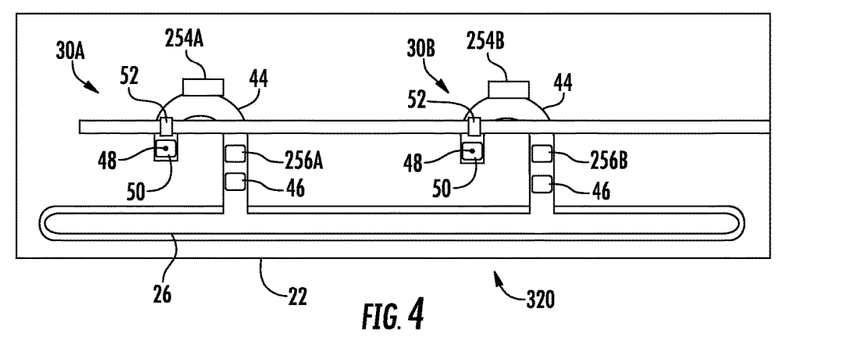
FIG. 4 is a schematic diagram of another example fluid testing device.

FIG. 4 schematically illustrates fluid testing device 320, another implementation of fluid testing device 20. Fluid testing device 320 is similar to fluid testing device 220 except that cells 30 additionally comprise detectors 256A, 256B (collectively referred to as counters 256). Detectors 256 comprise devices situated in or along microfluidic channels 44 between pumps 46 and discharge passage 48. In the example illustrated, detectors 256 are located between pumps 46 and photosensors 52. In one implementation, detectors 256 comprise devices to count number of cells, molecules or particles. In another implementation, detectors 256 comprise devices to sense or detect a size of such cells, molecules are particles. In one implementation, detectors 256 comprise impedance sensors that count or determine the size of cells, molecules or particles within microfluidic channel 44 by sensing changes in electrical impedance resulting from the flow of a fluid sample through or across an electric field region within microfluidic channel 44.

Figure 5:
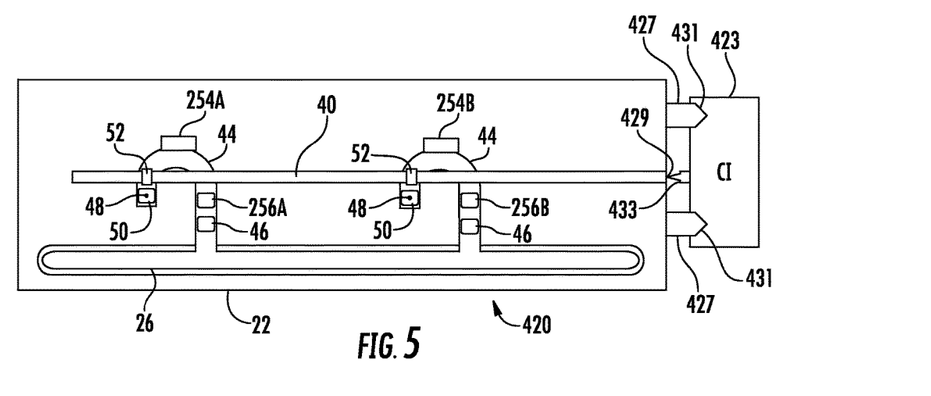
FIG. 5 is a schematic diagram of another example fluid testing device

FIG. 5 schematically illustrates fluid testing device 420, another implementation of fluid testing device 20. Fluid testing device 420 is similar to fluid testing device 320 except that fluid testing device 420 is provided as part of a coupon or cassette that is to be releasably connected to or mounted to a cassette interface 423. In the example illustrated, device 420 comprises electrical connectors 427 and optical input 429. Electrical connectors 427 make electrical contact with cassette interface 423. Electrical connectors 427 provide an electrical connection by which electrical power is supplied to device 420 and electrical data signals are transmitted between device 420 and interface 423. In the example illustrated, electrical connectors 427 comprise pins that are received within corresponding ports 431 of interface 423. Pins 427 mate with ports 431 to align optical input 429 with optical output 433 of cassette interface 423. Optical output 433 supplies light to light guide 40 for transmission to each of cells 30.

Although device 420 is illustrated as utilizing electrical connectors 427 which are plugged into ports 431 to align optical output 433 with optical input 429, in other implementations, other alignment mechanisms may be utilized to align optical output 433 with optical input 429 of device 420. For example, in other implementations, cassette interface 423 may comprise portions that are removably received or plugged into corresponding detents or ports of device 427. In one implementation, cassette interface 423 comprises a dongle which is itself fixedly or releasably connected to a computing device. In another implementation, cassette interface 423 is provided as part of a computing device.

Figure 6:
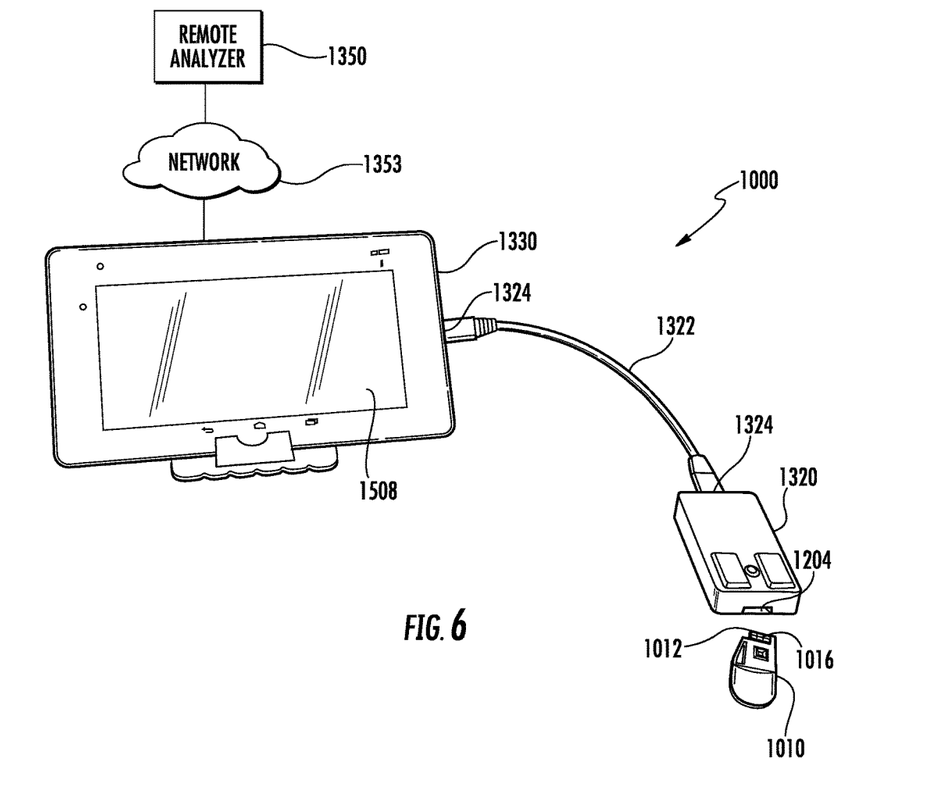
FIG. 6 is a schematic diagram of an example fluid testing system.

FIG. 6 illustrates an example microfluidic diagnostic or testing system 1000. System 1000 comprises a portable electronic device driven, impedance-based system by which samples of fluid, such as blood samples, are analyzed. The impedance of the fluid refers to the impedance of the fluid and/or any analyte in the fluid. System 1000, portions of which are schematically illustrated, comprises microfluidic cassette 1010, cassette interface 1320, mobile analyzer 1330 and remote analyzer 1350. Overall, microfluidic cassette 1010 receives a fluid sample and outputs signals based upon sensed characteristics of the fluid sample. Interface 1320 serves as an intermediary between mobile analyzer 1330 and cassette 1010. In the example illustrated, interface 1320 comprises a dongle releasably connected to mobile analyzer 1330 by a cable 1322 releasably or removably connected to interface 1320 at port 1324 and releasably or removably connected to mobile analyzer 1330 at port 1325. Interface 1320 removably connects to cassette 1010 and facilitates transmission of electrical power from mobile analyzer 1330 to cassette 1010 to operate pumps and sensors on cassette 1010. Interface 1320 further facilitates control of the pumps, eject, dispensers, and detectors or sensors on cassette 1010 by mobile analyzer 1330.

Mobile analyzer 1330 controls the operation cassette 1010 through interface 1320 and receives data produced by cassette 1010 pertaining to the fluid sample(s) being tested. Mobile analyzer 1330 analyzes data and produces output. Mobile analyzer 1330 further transmits processed data to remote analyzer 1350 across a wired or wireless network 1353 for further more detailed analysis and processing. In the example illustrated, mobile analyzer 1330 comprises a portable electronic device such as a smart phone, laptop computer, notebook computer, tablet computer or the like. As a result, system 1000 provides a portable diagnostic platform for testing fluid samples, such as blood samples.

Figures 7, 8A, 8B, 8C:
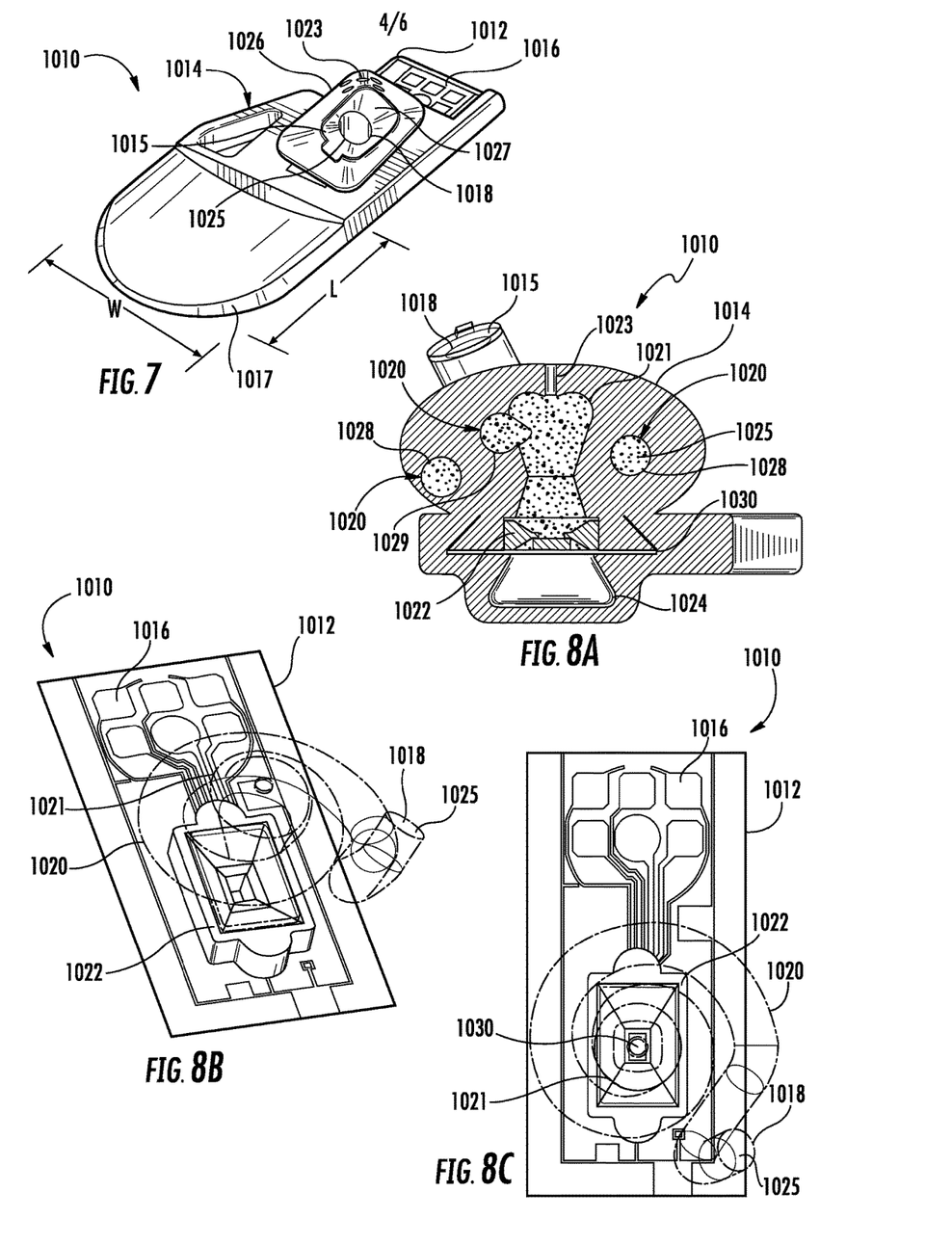
FIG. 7 is a perspective view of an example cassette.
FIG. 8A is a sectional view of the cassette of FIG. 7 with a modified exterior.
FIG. 8B is a perspective view of the cassette of FIG. 8A with portions omitted or shown transparently.
FIG. 8C is a top view of the cassette of FIG. 8A with portions omitted or shown transparently.
Figure 9A:
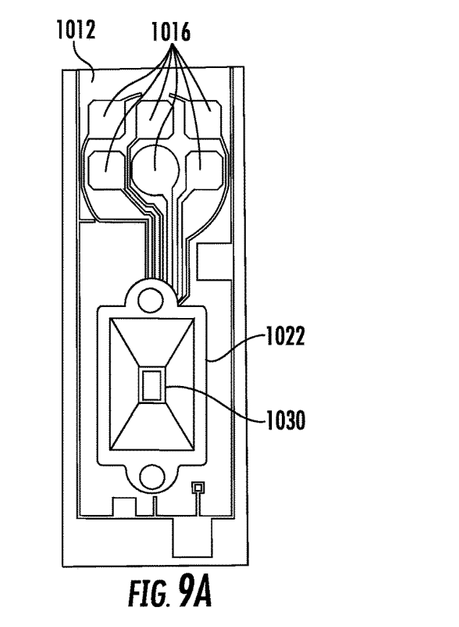
FIG. 9A is a top view of an example cassette board supporting an example microfluidic cassette and funnel.
Figure 9B:
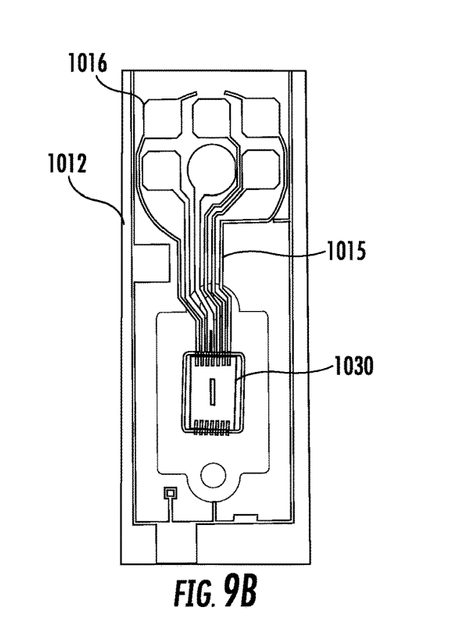
FIG. 9B is a bottom view of the cassette board of FIG. 9A.

FIGS. 7-12 illustrate microfluidic cassette 1010 in detail. As shown by FIGS. 7-9, cassette 1010 comprises cassette board 1012, cassette body 1014, membrane 1015 and microfluidic chip 1030. Cassette board 1012, shown in FIGS. 9A and 9B, comprises a panel or platform in which or upon which fluid chip 1030 is mounted. Cassette board 1012 comprises electrically conductive lines or traces 1015 which extend from electrical connectors of the microfluidic chip 1030 to electrical connectors 1016 on an end portion of cassette board 1012. As shown in FIG. 7, electrical connectors 1016 are exposed on an exterior cassette body 1014. As shown by FIG. 6, the exposed electrical connectors 1016 are to be inserted into interface 1320 so as to be positioned in electrical contact with corresponding electrical connectors within interface 1320, providing electrical connection between microfluidic chip 1030 and cassette interface 1320.

Cassette body 1014 partially surrounds cassette board 1012 so as to cover and protect cassette board 1012 and microfluidic chip 1030. Cassette body 1014 facilitates manual manipulation of cassette 1010, facilitating manual positioning of cassette 1010 into releasable interconnection with interface 1320. Cassette body 1014 additionally positions and seals against a person's finger during the acquisition of a fluid or blood sample while directing the received fluid sample to microfluidic chip 1030.

In the example illustrated, cassette body 1014 comprises finger grip portion 1017, sample receiving port 1018, residence passage 1020, sample holding chamber 1021, chip funnel 1022, vent 1023 and discharge reservoir 1024. Finger grip portion 1017 comprises a thin portion of body 1014 opposite to the end of cassette 1010 at which electrical connectors 1016 are located. Finger grip portion 1017 facilitates gripping of cassette 1010 in connection or insertion of cassette 1010 into a receiving port 1204 of cassette interface 1320 (shown in FIG. 7). In the example illustrated, finger grip portion 1017 has a width W of less than or equal to 2 inches, a length L of less than or equal to 2 inches and a thickness of less than or equal to 0.5 inches.

Sample receiving port 1018 may comprise an opening into which a fluid sample, such as a blood sample, is to be received. In the example illustrated, sample receiving port 1018 has a mouth 1025 that is formed on a top surface 1027 of an elevated platform or mound 1026 that extends between finger grip portion 1017 and the exposed portion of cassette board 1012. Mound 1026 clearly identifies the location of sample receiving port 1018 for the intuitive use of cassette 1010. In one implementation, the top surface 1027 is curved or concave to match or approximately match the lower concave surface of a finger of a person so as to form an enhanced seal against the bottom of the person's finger from which the sample is taken. Capillary action pulls in blood from the finger which forms the sample. In one implementation, the blood sample is of 5 to 10 microliters. In other implementations, port 1018 is located at alternative locations or mound 1026 is omitted, for example, as depicted in FIG. 8A. Although FIG. 8A illustrates cassette 1010 having a slightly different outer configuration for cassette body 1014 as compared to body 1014 shown in FIG. 7, wherein the cassette body 1014 shown in FIG. 8A omits mound 1026, those remaining elements or components shown in FIGS. 7 and 8A are found in both of the cassette bodies shown in FIGS. 7 and 8A.

As shown by FIGS. 8A-8C, residence passage 1020 comprises a fluid channel, conduit, tube or other passage extending between sample input port 1018 and sample holding chamber 1021. Residence passage 1020 extends between sample input port 1018 and sample holding chamber 1021 in a tortuous fashion, an indirect or non-linear fashion full of twists and turns, to lengthen the time for a received sample, input through sample input port 1018, to travel or flow to chip 1030. Residence passage 1018 provides a volume in which the fluid sample being tested and a fluid reagent may mix prior to reaching chip 1030. In the example illustrated, residence passage 263 is circuitous, comprising a circular or helical passage winding in the space of cassette body 1012 between port 1018 and chip 1030. In another implementation, residence passage 1020 twists and turns, zigzags, snakes, serpentines and/or meanders in a zigzag fashion within the space between sample input port 1018 and chip 1030.

In the example illustrated, residence passage 1020 extends in a downward direction towards microfluidic chip 1030 (in the direction of gravity) and subsequently extends in an upward direction away from microfluidic chip 1030 (in a direction opposite to that of gravity). For example, as shown by FIGS. 8A and 8B, upstream portions 1028 extend vertically below the downstream end portion 1029 of residence passage 1020 that is adjacent to and directly connected to sample holding chamber 1021. Although upstream portions receive fluid from input port 1018 before end portion 1029, end portion 1029 is physically closer to input port 1018 in a vertical direction. As a result, fluid flowing from the upstream portions flows against gravity to the downstream or end portion 1029. As described hereafter, in some implementations, residence passage 1020 contains a reagent 1025 which reacts with the fluid sample or blood sample being tested. In some circumstances, this reaction may produce residue or fallout. For example, a fluid sample such as blood that has undergone lysis will have lysed cells or lysate. Because end portion 1029 of residence passage 1020 extends above upstream portions 1028 of residence passage 1020, such residue or fallout resulting from the reaction of the fluid sample with reagent 1025 settles out and is trapped or retained within such upstream portions 1028. In other words, the amount of such residue or fallout passing through residence passage 1020 to microfluidic chip 1030 is reduced. In other implementations, residence passage 1020 extends in a downward direction to sample holding chamber 1021 throughout its entire course.

Sample holding chamber 1021 may comprise a chamber or internal volume in which the fluid sample or blood sample being tested collects above chip 1030. Chip funnel 1022 comprises a funneling device that narrows down to chip 1030 so as to funnel the larger area of chamber 1021 to the smaller fluid receiving area of chip 1030. In the example illustrated, sample input port 1018, residence passage 1020, sample holding chamber 1021 and chip funnel 1022 form an internal fluid preparation zone in which a fluid or blood sample may be mixed with a reagent before entering chip 1030. In one implementation, the fluid preparation zone has a total volume of 20 to 250 µL. In other implementations, the fluid preparation zone provided by such internal cavities may have other volumes.

As indicated by stippling in FIG. 8A, in one implementation, cassette 1010 is prefilled with a fluid reagent 1025 prior to insertion of a sample fluid to be tested into port 1018. Fluid reagent 1025 may comprise a composition that interacts with the fluid to be tested, enhancing the ability of microfluidic chip 130 to analyze a selected characteristic or a group of selected characteristics of the fluid to be tested. In one implementation, fluid reagent 1025 comprises a composition to dilute the fluid being tested. In one implementation, fluid reagent 1025 comprises a composition to perform lysis on the fluid or blood being tested. In yet another implementation, fluid reagent 264 comprises a composition to facilitate tagging of selected portions of the fluid being tested. For example, in one implementation, fluid reagent 1025 comprises magnetic beads, gold beads or latex beads. In other implementations, fluid reagent 1025 comprises other liquid or solid compositions or liquids, distinct from the sample fluid to be tested, that interact with or that modify the sample fluid placed within sample input port 1018 prior to the sample fluid being received, processed and analyzed by microfluidic chip 1030.

Vents 1023 may comprise passages communicating between sample holding chamber 1021 and the exterior of cassette body 1014. In the example illustrated in FIG. 7, vents 1023 extend through the side of mount 1026. Vents 1023 are sized small enough to retain fluid within sample holding chamber 1021 through capillary action but large enough so as to permit air within holding chamber 1021 to escape as holding chamber 1021 is filled with fluid. In one implementation, each of their vents has an opening or diameter of 50 to 200 micrometers.

Discharge reservoir 1024 may comprise a cavity or chamber within body 1014 arranged to receive fluid discharged from chip 1030. Discharge reservoir 1024 is to contain fluid that has been passed through chip 1030 and that has been processed or tested. Discharge reservoir 1024 may receive processed or tested fluid such that the same fluid is not tested multiple times. In the example illustrated, discharge reservoir 1024 is formed in body 1014 below chip 1030 or on a side of chip 1030 opposite to that of chip funnel 1022 and sample holding chamber 1021 such that chip 1030 is sandwiched between chip funnel 1022 and discharge reservoir 1024. In one implementation, discharge reservoir 1024 is completely contained within body 1014 and is inaccessible (but through the destruction of body 1014 such as by cutting, drilling or other permanent destruction or breaking of body 1014), locking the processed or tested fluid within body 112 for storage or subsequent sanitary disposal along with disposal of cassette 1010. In yet another implementation, discharge reservoir 1024 is accessible through a door or septum, allowing processed or tested fluid to be withdrawn from reservoir 1020 for further analysis of the tested fluid, for storage of the tested fluid in a separate container or for emptying of reservoir 1024 to facilitate continued use of cassette 1010.

In some implementations, microfluidic reservoir 1024 is omitted. In such implementations, those portions of the fluid samples or blood samples that have been tested are processed by microfluidic chip 1030 are recirculated back to an input side or input portion of microfluidic chip 1030. For example, in one implementation, microfluidic chip 1030 comprises a microfluidic reservoir which receives fluid through chip funnel 1022 on a input side of the sensor or sensors provided by microfluidic chip 1030. Those portions of a fluid sample or blood sample that have been tested are returned back to the microfluidic reservoir on the input side of the sensor or sensors of microfluidic chip 1030.

Membrane 1015 may comprise an imperforate, liquid impermeable panel, film or other layer of material adhesively are otherwise secured in place so as to extend completely across and completely cover mouth 1025 of port 1018. In one implementation, membrane 1015 serves as a tamper indicator identifying if the interior volume of cassette 1010 and its intended contents have been compromised or tampered with. In implementations where the sample preparation zone of cassette 1010 has been prefilled with a reagent, such as reagent 1025 described above, membrane 1015 seals the fluid reagent 1025 within the fluid preparation zone, within port 1018, residence passage 1020, fluid holding chamber 1021 and chip funnel 1022. In some implementations, membrane 1015 additionally extends across vents 1023. In some implementations, membrane 1015 is additionally gas or air impermeable.

In the example illustrated, membrane 1015 seals or contains fluid reagent 1025 within cassette 1010 at least until the fluid sample is to be deposited into sample input port 1018. At such time, membrane 1015 may be peeled away, torn or punctured to permit insertion of the fluid sample through mouth 1018. In other implementations, membrane 1015 may comprise septum through which a needle is inserted to deposit a fluid or blood sample through mouth 1018. Membrane 1015 facilitates pre-packaging of fluid reagent 1025 as part of cassette 1010, wherein the fluid agent 1025 is ready for use with the subsequent deposits of the fluid sample to be tested. For example, a first cassette 1010 containing a first fluid reagent 1025 may be predesigned or designated for testing a first characteristic of a first sample of fluid while a second cassette 1010 containing a second fluid reagent 1025, different than the first fluid reagent 1025, may be predesigned or designated for testing a second characteristic of a second sample of fluid. In other words, different cassettes 1010 may be specifically designed for testing different characteristics depending upon the type or a quantity of fluid reagent 1025 contained therein.

Figure 10:
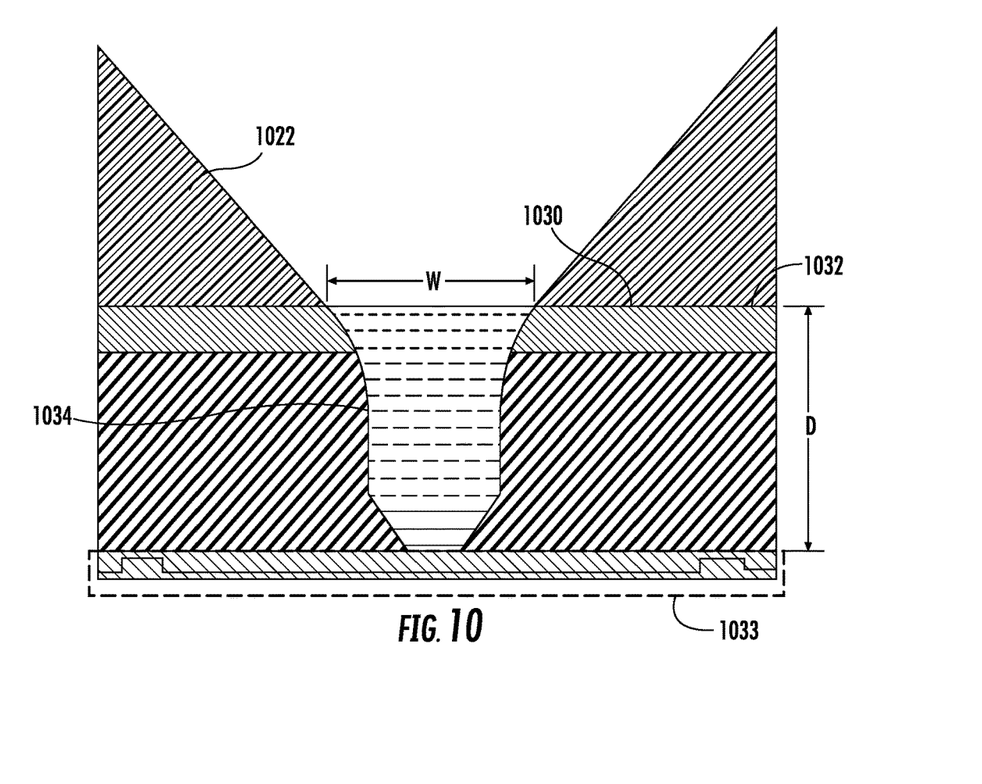
FIG. 10 is a fragmentary sectional view of a portion of the cassette board of FIG. 9A.
Figure 11:
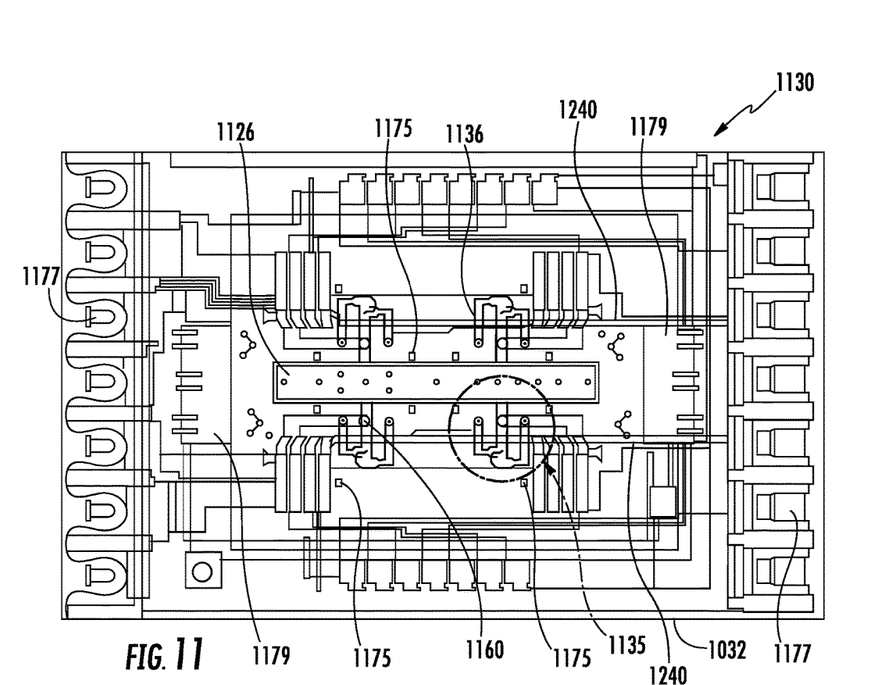
FIG. 11 is a top view of another example of the microfluidic chip of the cassette of FIGS. 7 and 8A.

FIGS. 9A, 9B and 10 illustrate microfluidic chip 1030. FIG. 9A illustrates a top side of cassette board 1012, chip funnel 1022 and microfluidic chip 1030. FIG. 9A illustrates microfluidic chip 1030 sandwiched between chip funnel 1022 and cassette board 1012. FIG. 9B illustrate a bottom side of the set board 1012 and microfluidic chip 1030. FIG. 10 is a cross-sectional view of microfluidic chip 1030 below chip funnel 1022. As shown by FIG. 11, microfluidic chip 1030 comprises a substrate 1032 that comprises, or is formed from, a material such as silicon. Microfluidic chip 1030 comprises a microfluidic reservoir 1034 formed in substrate 1032 and which extends below chip funnel 1022 to receive the fluid sample (with a reagent in some tests) into chip 1030. In the example illustrated, microfluidic reservoir has a mouth or top opening having a width VV of less than 1 mm and nominally 0.5 mm. Reservoir 1034 has a depth D of between 0.5 mm and 1 mm and nominally 0.7 mm. As will be described hereafter, microfluidic chip 1030 comprises pumps and sensors along a bottom portion of chip 1030 in region 1033.

Figure 12:
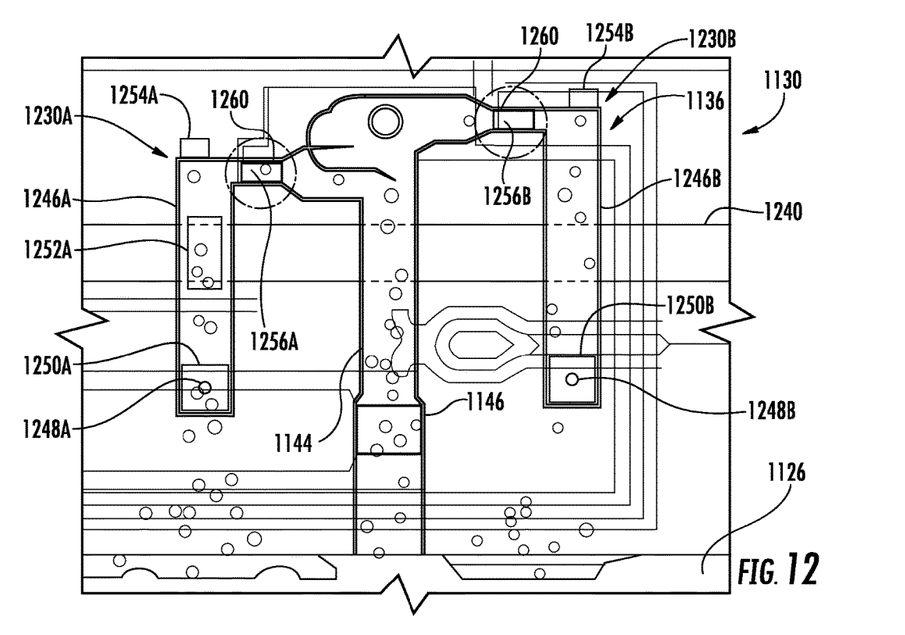
FIG. 12 is an enlarged fragmentary top view of an example sensing region of the microfluidic chip of FIG. 12.

FIGS. 11 and 12 are enlarged views of microfluidic chip 1130, an example implementation of microfluidic chip 1030. Microfluidic chip 1130 integrates each of the functions of fluid pumping and impedance sensing on a low-power platform. As shown by FIG. 11, microfluidic chip 1030 comprises substrate 1032 in which is formed slot 1126. In addition, microfluidic chip 1130 comprises multiple sensing regions 1135, wherein each sensing region provides a pair of testing cells 1230A, 1230B (collectively referred to as testing cells 1230) that share a pump. As shown by FIGS. 11 and 12, each of the testing cells 1230 of multiple sensing regions 1135 are provided with light from a single light guide 1240.

FIG. 12 is an enlarged view illustrating one of sensing regions 1135 of chip 1130 shown in FIG. 11. As shown by FIG. 12, sensing region 1135 comprises microfluidic channel 1244, pump 1246, branch channels 1246A, 1246B, discharge passages 1248A, 1248B, fluid dischargers 1250A, 1250B, photosensors 1252A, 1252B, tagging dispensers 1254A, 1254B and detectors 1256A, 1256B. Microfluidic channel 1244 comprises a passage extending within or formed within substrate 1032 for the flow of a fluid sample from slot 1126.

Pump 1146 is similar to pump 46 described above. Pump 1146 pumps are moves fluid from slot 1126 into each of branch channels 1246. In one implementation, pump 1146 comprises a bubble jet inertial pump. In other implementations, pump 1146 may comprise other microfluidic pumping devices.

Branch channel 1246A, discharge passage 1248A, fluid discharger 1250A, photosensor 1252A, tagging dispenser 1254A and detector 1256 form a first testing cell 1230A. Similarly, branch channel 1246B, discharge passage 1248B, fluid discharger 1250B, photosensor 1252B, tagging dispenser 1254B and detector 1256B form a second testing cell 1230B.

Discharge passages 1248A and 1248B extend from microfluidic channel 1144 to fluid discharge passages 1248A and 1248B, respectively. Each of branch portions 1248 comprises a narrowing portion, throat or constriction 1260 through with the fluid flows. For purposes of this disclosure, a "constriction" means any narrowing in at least one dimension. A "constriction" may be formed by (A) one side of a channel having a protruberance projecting towards the other side of the channel, (B) both sides of a channel having at least one protruberance projecting towards the other side of the channel, wherein such multiple protruberances are either aligned with one another or are staggered along the channel or (C) at least one column or pillar projecting between two walls of the channel to discriminate against what can or cannot flow through the channel. In other implementations, constrictions 1260 may be omitted.

In one implementation, branch channels 1246 are similar to one another. In another implementation, branch channels 1246 are shaped or dimensioned different from one another so as to facilitate different fluid flow characteristics. For example, the constrictions 1260 or other regions of channels 1246 may be differently sized such that particles or cells of a first size more readily flow through, if at all, through one of channels 1246 as compared to the other of channels 1246. Because channels 1246 diverge from opposite sides of channel 1144, both of channels 1246 receive fluid directly from channel 1144 without fluid being siphoned to any other portions beforehand.

Discharge passages 1248 may comprise fluid conduits through which fluid or the fluid sample is discharged from the respective branch channel 1246. In one implementation, discharge passages 1248 direct or guide fluid to discharge reservoir 1024 (shown in FIG. 8A). In yet other implementations, discharge passages 1248 direct or guide fluid to other microfluidic channels or passages of additional testing devices. In still other implementations, discharge passages 1248 direct or guide fluid into trays, partitioned containers or onto a test strip. In one implementation, each of discharge passages 1248 comprises a nozzle through which fluid is uni-directionally ejected from the respective channel 1246. In another implementation, each discharge passage 1248 comprises a valve through which fluid is selectively guided or ejected.

Fluid dischargers 50 may comprise devices to selectively move and discharge fluid from the respective channel 1246 through discharge passage 1248. In one implementation, fluid discharger 1250 comprises a drop-on-demand fluid ejection device such as a thermal inkjet resistor which nuclease fluid to create a bubble to forcefully expeller eject fluid through discharge passage 1248. In another implementation, fluid discharger 1250 comprises a drop on demand fluid ejection device such as a piezo resistive device that changes shape or vibrates in response to applied electrical current to move a diaphragm to thereby eject adjacent fluid through discharge passage 1248. In still other implementations, fluid discharger 1250 may comprise other devices to selectively and forcibly eject fluid through discharge passage 1248.

Photosensor 1252 may comprise an optical sensor situated in our along an associated branch channel 1246. Each photosensor 1252 senses interaction of light with the analyte and/or solution containing the analyte within the respective channel 1246. In response to sense interactions of light with the analyte or solution, each photosensor 1252 may output electrical signals which vary based upon such interactions, wherein the electrical signals are analyzed and indicate characteristics of the fluid sample that interacted with a light.

Fluid tagging dispensers 1254 comprise devices located along microfluidic channels 1246 that dispense tags to mark particular cells or molecules of interest. In the example illustrated, dispensers 1254 are located upstream of photosensor 1252, between photosensor 1252 and the inlet of respective branch channel 1246. In one implementation, fluid tagging dispensers 1254 dispense fluorescent powder which tags molecules of interest. Such tagging facilitates reading by photosensor 1252, wherein the light being transmitted by light guide 1240 excites fluorescent powder or tags facilitate detection by photosensor 1252. In one implementation, each of dispensers 1254 dispense a different fluorescent marker to differently tag different molecules, particles or cells, facilitating multiple tests being performed at the same time the same initial sample supplied to slot 1226. In another implementation, dispensers 1254 dispense the same fluorescent marker. In one implementation, pumps 1246 concentrate the fluid samples within microfluidic channels 1246 before ejection to facilitate gathering of a sufficient amount or number of tagged molecules for sensing and analysis. In some implementations, dispensers 1254 may be omitted.

Detectors 1256 each may comprise a micro-fabricated device formed upon substrate 1032 within constriction 1260. In one implementation, each injector 1256 comprises a micro-device that is designed to output electrical signals or cause changes in electrical signals that indicate properties, parameters or characteristics of the fluid and/or cells/particles of the fluid passing through constriction 1260. In one implementation, each of detectors 1256 comprises a cell/particle sensor that detects properties of cells or particles contained in a fluid and/or that detects the number of cells or particles in fluid passing across detector 1256. For example, in one implementation, detector 1256 comprises an electric sensor which outputs signals based upon changes in electrical impedance brought about by differently sized particles or cells flowing through constriction 1260 and impacting impedance of the electrical field across or within constriction 1260. In one implementation, sensor 1138 comprises an electrically charged high side electrode and a low side electrode formed within or integrated within a surface of channel 1246 within constriction 1260. In one implementation, the low side electrode is electrically grounded. In another implementation, low side electrode comprises a floating low side electrode. For purposes of this disclosure, a "floating" low side electrode refers to an electrode having all connecting admittances zero. In other words, the floating electrode is disconnected, not being connected to another circuit or to earth. In some implementations, detectors 1256 may be omitted.

Light guide 1240 comprises a light guiding and directing structure that is to receive light from interface 1202 serially transmit light or electromagnetic radiation to the microfluidic channel of each of the testing cells 1230. In the example illustrated, when cassette 1010 is inserted into port 1204 of interface 1320, an optical light source of interface 1320 becomes aligned with each of the light guides 1240 of cassette 1010. In the example illustrated, each of testing cells 1230 are sufficiently aligned with one another such that light guide 1240 extends across each of such microfluidic channels 1246, providing light or electromagnetic radiation to each of cells 30 for interacting with the fluid contained within each of cells 1230 and for detection by photosensors 1252. Because light guide 1240 supplies electromagnetic radiation are light to each of the multiple cells 1230, real estate upon the chip 1130 is conserved, allowing chip 1130 and cassette 1010 to be more compact. In addition, the complexity and cost of cassette 1010 may also be reduced through the use of a single light guide 1240 supplying light to each of the individual testing cells 1230.

In the example illustrated, light guide 1240 comprises a waveguide or light pipe that linearly extends across microfluidic channel 44 of each of its associated testing cells 1230. In other implementations, light guide 1240 may extend in a serpentine fashion or a bent or arcuate fashion when serially extending from one fluid testing cell 1230 to another fluid testing cell 1230.

Although the present disclosure has been described with reference to example implementations, workers skilled in the art will recognize that changes may be made in form and detail without departing from the spirit and scope of the claimed subject matter. For example, although different example implementations may have been described as including one or more features providing one or more benefits, it is contemplated that the described features may be interchanged with one another or alternatively be combined with one another in the described example implementations or in other alternative implementations. Because the technology of the present disclosure is relatively complex, not all changes in the technology are foreseeable. The present disclosure described with reference to the example implementations and set forth in the following claims is manifestly intended to be as broad as possible. For example, unless specifically otherwise noted, the claims reciting a single particular element also encompass a plurality of such particular elements.

What is claimed is:

1. An apparatus comprising:
   a body forming a slot;
   testing cells along a length of the slot, each testing cell comprising:
   a microfluidic channel extending from the slot;
   a pump to move fluid from the slot into the channel;
   a discharge passage through which fluid exits the channel;
   a fluid discharger to discharge fluid from the channel through the discharge passage;
   a fluid tagging dispenser; and
   a photosensor; and
   a light guide to receive light from an external light source and serially transmit the light to the microfluidic channel of each of the testing cells.

2. The apparatus of claim 1, wherein the light guide extends across the microfluidic channel.

3. The apparatus of claim 1, wherein the testing cells are on one side of the slot.

4. The apparatus of claim 1, wherein the pump comprises a thermal inkjet resister inertial pump.

5. The apparatus of claim 1, wherein the fluid discharger comprises a thermal inkjet resister.

6. The apparatus of claim 1, wherein each fluid tagging dispenser is to dispense a different tagging material.

7. A fluid testing cassette comprising:
   a body having a plug portion to removably connect to a cassette interface;
   a slot within the body to receive fluid being tested;
   testing cells along a length of the slot, each testing cell comprising:
   a microfluidic channel extending from the slot;
   a pump to move fluid from the slot into the channel;
   a discharge nozzle through which fluid exits the channel;
   a fluid discharger to discharge fluid from the channel through the nozzle; and
   a photosensor; and
   a light guide on and extending from the plug portion to receive light from the cassette interface and serially transmit the light to the microfluidic channel of each of the testing cells.

8. The fluid testing cassette of claim 7 further comprising electrical contacts on the plug portion to electrically connect the fluid testing cassette to the cassette interface.

9. The fluid testing cassette of claim 7, the plug portion is removably received within a port of the cassette interface.

10. The fluid testing cassette of claim 7, wherein the light guide serially transmits the light from the cassette interface to the microfluidic channel of each of the testing cells.

11. The fluid testing cassette of claim 7, wherein the pump comprises a thermal inkjet resister inertial pump.

12. The fluid testing cassette of claim 7, wherein the fluid discharger comprises a thermal inkjet resister.

13. A method comprising:
depositing a fluid sample in a slot of a body;
pumping a portion of the fluid sample in the slot into each of a plurality of channels of testing cells along a length of the slot;
transmitting light from an external light source serially across each of the plurality of channels;
sensing interaction of the transmitted light with the portion of the fluid sample in each of the plurality of channels;
ejecting the portion of the fluid sample from each of the plurality of channels;
determining a number of cells in the portion of the fluid sample within each of the plurality of channels; and
pumping additional fluid of the fluid sample from the slot into each of the plurality of channels based upon the determined number of cells in the portion of the fluid sample within each of the plurality of channels.

14. The apparatus of claim 1, wherein the microfluidic channel of each of the slots is formed in the body and branches off from the slot.

15. An apparatus comprising:
a body forming a slot;
testing cells along a length of the slot, each testing cell comprising:
a microfluidic channel extending from the slot;
a pump to move fluid from the slot into the channel;
a discharge passage through which fluid exits the channel;
a fluid discharger to discharge fluid from the channel through the discharge passage; and
a photosensor; and
a light guide to receive light from an external light source and serially transmit the light to the microfluidic channel of each of the testing cells;
wherein each microfluidic channel has a U-shape and wherein the light guide crosses the microfluidic channel twice.

16. The apparatus of claim 1, wherein each testing cell further comprises a detector to count a number of cells, molecules or particles.

17. The apparatus of claim 1, wherein each testing cell further comprises an impedance sensor that senses changes in electrical impedance resulting from fluid flow within the microfluidic channel.

18. The apparatus of claim 1, wherein the body comprises a circuit chip comprising electronic componentry and electrical conductors.

* * * * *

UNITED STATES PATENT AND TRADEMARK OFFICE
CERTIFICATE OF CORRECTION

PATENT NO. : 10,401,280 B2
APPLICATION NO. : 15/570958
DATED : September 3, 2019
INVENTOR(S) : Timothy L. Weber It is certified that error appears in the above-identified patent and that said Letters Patent is hereby corrected as shown below:

On the Title Page

In item (73), Assignee, in Column 1, Line 1, delete "Hewett" and insert --Hewlett--, therefor.

Signed and Sealed this
Thirty-first Day of December, 2019

Andrei Iancu
*Director of the United States Patent and Trademark Office*